(12) United States Patent
Klofta (10) Patent No.: US 9,468,565 B2
(45) Date of Patent: Oct. 18, 2016

(54) ABSORBENT ARTICLES COMPRISING WETNESS INDICATORS

(71) Applicant: The Procter & Gamble Company, Cincinnati, OH (US)

(72) Inventor: Thomas James Klofta, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 74 days.

(21) Appl. No.: 14/567,021

(22) Filed: Dec. 11, 2014

(65) Prior Publication Data
US 2015/0094676 A1   Apr. 2, 2015

Related U.S. Application Data

(63) Continuation of application No. 12/758,165, filed on Apr. 12, 2010, now Pat. No. 8,927,801.

(60) Provisional application No. 61/168,756, filed on Apr. 13, 2009.

(51) Int. Cl.
| | | |
|---|---|---|
| A61F 13/15 | (2006.01) | |
| A61F 13/42 | (2006.01) | |
| A61F 13/532 | (2006.01) | |
| A61F 13/536 | (2006.01) | |
| A61F 5/44 | (2006.01) | |
| A61F 13/49 | (2006.01) | |
| A61F 13/514 | (2006.01) | |

(52) U.S. Cl.
CPC .............. *A61F 13/42* (2013.01); *A61F 13/536* (2013.01); *A61F 13/5323* (2013.01); *A61F 5/44* (2013.01); *A61F 13/49* (2013.01); *A61F 13/514* (2013.01); *A61F 2013/422* (2013.01); *A61F 2013/425* (2013.01); *A61F 2013/427* (2013.01)

(58) Field of Classification Search
CPC ........ A61F 5/44; A61F 13/49; A61F 13/514; A61F 13/42
USPC .......................... 604/360, 361, 359, 366, 367
See application file for complete search history.

(56) References Cited

U.S. PATENT DOCUMENTS

| | | |
|---|---|---|
| 3,563,243 A | 2/1971 | Lindquist |
| 3,860,003 A | 1/1975 | Buell |

(Continued)

FOREIGN PATENT DOCUMENTS

| | | |
|---|---|---|
| EP | 148115 A1 | 7/1985 |
| EP | 0818569 A2 | 1/1998 |

(Continued)

OTHER PUBLICATIONS

ISR and Written Opinion, PCT/US2010/030791, date of mailing Jul. 29, 2010.

(Continued)

*Primary Examiner* — Jacqueline Stephens
(74) *Attorney, Agent, or Firm* — Richard L. Alexander (57) ABSTRACT

An absorbent article of the present invention may comprise a backsheet, a wetness indicator composition, and an absorbent core. The wetness indicator composition may comprise a stabilizer, a colorant, and a matrix. The absorbent core may comprise a nonwoven layer and an absorbent polymer material, and optionally, a thermoplastic adhesive material. The wetness indicator composition may be in direct contact with an inner surface of the backsheet and an outer surface of the nonwoven layer. And, the absorbent polymer material, and optionally, the thermoplastic adhesive material, may be in direct contact with an inner surface of the nonwoven. Further, the absorbent core may be substantially cellulose free and may be oriented in at least one row.

21 Claims, 1 Drawing Sheet

(56) References Cited

U.S. PATENT DOCUMENTS

| | | |
|---|---|---|
| 3,911,173 A | 10/1975 | Sprague, Jr. |
| 3,929,135 A | 12/1975 | Thompson |
| 4,324,246 A | 4/1982 | Mullane et al. |
| 4,334,920 A | 6/1982 | Mori et al. |
| 4,342,314 A | 8/1982 | Radel et al. |
| 4,463,045 A | 7/1984 | Ahr et al. |
| 4,573,986 A | 3/1986 | Minetola et al. |
| 4,609,518 A | 9/1986 | Curro et al. |
| 4,610,678 A | 9/1986 | Weisman et al. |
| 4,623,340 A | 11/1986 | Luceri |
| 4,629,643 A | 12/1986 | Curro et al. |
| 4,636,207 A | 1/1987 | Buell |
| 4,673,402 A | 6/1987 | Weisman et al. |
| 4,681,578 A | 7/1987 | Anderson et al. |
| 4,695,278 A | 9/1987 | Lawson |
| 4,704,115 A | 11/1987 | Buell |
| 4,704,116 A | 11/1987 | Enloe |
| 4,740,520 A | 4/1988 | Hallenbach et al. |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,888,231 A | 12/1989 | Angstadt |
| 4,892,536 A | 1/1990 | Desmarais et al. |
| 4,900,317 A | 2/1990 | Buell |
| 4,909,803 A | 3/1990 | Aziz et al. |
| 4,940,464 A | 7/1990 | Van Gompel et al. |
| 4,950,254 A | 8/1990 | Andersen et al. |
| 4,988,344 A | 1/1991 | Reising et al. |
| 4,990,147 A | 2/1991 | Freeland |
| 4,998,345 A | 3/1991 | Funahashi et al. |
| 5,006,394 A | 4/1991 | Baird |
| 5,037,416 A | 8/1991 | Allen et al. |
| 5,085,654 A | 2/1992 | Buell |
| 5,092,861 A | 3/1992 | Nomura et al. |
| 5,147,345 A | 9/1992 | Young et al. |
| 5,151,092 A | 9/1992 | Buell et al. |
| 5,221,274 A | 6/1993 | Buell et al. |
| 5,234,423 A | 8/1993 | Alemany et al. |
| 5,246,433 A | 9/1993 | Hasse et al. |
| 5,260,345 A | 11/1993 | Desmarais et al. |
| 5,269,775 A | 12/1993 | Freeland et al. |
| 5,342,338 A | 8/1994 | Roe |
| 5,492,751 A | 2/1996 | Butt, Sr. et al. |
| 5,507,760 A | 4/1996 | Wynne et al. |
| 5,554,145 A | 9/1996 | Roe et al. |
| 5,562,646 A | 10/1996 | Goldman et al. |
| 5,569,234 A | 10/1996 | Buell et al. |
| 5,580,411 A | 12/1996 | Nease et al. |
| H1630 H | 1/1997 | Roe et al. |
| 5,599,335 A | 2/1997 | Goldman et al. |
| 5,607,760 A | 3/1997 | Roe |
| 5,609,587 A | 3/1997 | Roe |
| 5,628,097 A | 5/1997 | Benson et al. |
| 5,635,191 A | 6/1997 | Roe et al. |
| H1670 H | 7/1997 | Aziz et al. |
| 5,643,588 A | 7/1997 | Roe et al. |
| 5,669,894 A | 9/1997 | Goldman et al. |
| 5,743,946 A | 4/1998 | Aoki et al. |
| 5,766,389 A | 6/1998 | Brandon et al. |
| 5,769,838 A | 6/1998 | Buell et al. |
| 5,897,545 A | 4/1999 | Kline et al. |
| 5,899,895 A | 5/1999 | Robles et al. |
| 5,899,896 A | 5/1999 | Suprise et al. |
| 5,916,661 A | 6/1999 | Benson et al. |
| 5,941,864 A | 8/1999 | Roe |
| 5,957,908 A | 9/1999 | Kline et al. |
| 5,967,665 A | 10/1999 | MacDonald et al. |
| 5,968,025 A | 10/1999 | Roe et al. |
| 6,004,306 A | 12/1999 | Robles et al. |
| 6,075,178 A | 6/2000 | LaWilhelm et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,297,424 B1 | 10/2001 | Olson et al. |
| 6,307,119 B1 | 10/2001 | Cammarota et al. |
| 6,414,215 B1 | 7/2002 | Roe |
| 6,476,288 B1 | 11/2002 | Vanrijswijck et al. |
| 6,545,197 B1 | 4/2003 | Muller et al. |
| 6,596,918 B1 | 7/2003 | Wehrle et al. |
| 6,627,786 B2 | 9/2003 | Roe et al. |
| 6,627,787 B1 | 9/2003 | Roe et al. |
| 6,653,522 B1 | 11/2003 | Blumenthal |
| 6,680,422 B2 | 1/2004 | Roe |
| 6,710,221 B1 | 3/2004 | Pierce et al. |
| 6,719,742 B1 | 4/2004 | McCormack et al. |
| 6,743,314 B2 | 6/2004 | Henry et al. |
| 6,772,708 B2 | 8/2004 | Klofta |
| 6,790,798 B1 | 9/2004 | Suzuki et al. |
| 6,904,865 B2 | 6/2005 | Klofta |
| 6,932,798 B2 | 8/2005 | Kudo et al. |
| 6,972,010 B2 | 12/2005 | Pesce et al. |
| 7,159,532 B2 | 1/2007 | Klofta |
| 7,332,642 B2 | 2/2008 | Liu |
| 8,080,704 B2 | 12/2011 | Uchida |
| 8,348,920 B2 | 1/2013 | Liu |
| 8,618,349 B2 | 12/2013 | Klofta |
| 2002/0017376 A1 | 2/2002 | Geltser et al. |
| 2003/0073966 A1 | 4/2003 | Sosalla et al. |
| 2003/0233082 A1 | 12/2003 | Kline et al. |
| 2004/0015145 A1 | 1/2004 | Miura et al. |
| 2004/0097895 A1 | 5/2004 | Busam et al. |
| 2004/0138633 A1 | 7/2004 | Mishima et al. |
| 2004/0158212 A1 | 8/2004 | Ponomarenko et al. |
| 2004/0158213 A1 | 8/2004 | Ponomarenko et al. |
| 2004/0158214 A1 | 8/2004 | Ponomarenko et al. |
| 2005/0043438 A1 | 2/2005 | Moore et al. |
| 2005/0148961 A1 | 7/2005 | Sosalla et al. |
| 2005/0177123 A1 | 8/2005 | Catalan |
| 2005/0199177 A1 | 9/2005 | Klofta et al. |
| 2005/0234414 A1 | 10/2005 | Liu |
| 2005/0234415 A1 | 10/2005 | Liu |
| 2006/0149197 A1 | 7/2006 | Niemeyer |
| 2006/0149204 A1 | 7/2006 | Niemeyer |
| 2008/0312618 A1 | 12/2008 | Hundorf |
| 2008/0312625 A1 | 12/2008 | Hundorf |
| 2009/0012491 A1 | 1/2009 | D'Addario et al. |

FOREIGN PATENT DOCUMENTS

| | | |
|---|---|---|
| EP | 1522802 A1 | 4/2005 |
| EP | 1547560 A1 | 6/2005 |
| EP | 1216673 B1 | 10/2005 |
| EP | 1591091 A2 | 11/2005 |
| JP | 57-118289 | 7/1982 |
| JP | 58-114772 | 7/1983 |
| JP | 59-024704 | 2/1984 |
| JP | 60-020509 | 2/1985 |
| JP | 61-137606 U | 8/1986 |
| JP | 1-250843 | 10/1989 |
| JP | 4-15999 U | 2/1992 |
| JP | 2003-210522 | 7/2003 |
| JP | 2004-049405 | 2/2004 |
| JP | 2008-284183 A | 11/2008 |
| WO | WO-9524173 | 9/1995 |
| WO | WO0069382 A1 | 11/2000 |
| WO | WO-01-41691 | 6/2001 |
| WO | WO-02-26177 | 4/2002 |
| WO | WO2004/006818 | 1/2004 |
| WO | WO-2006073522 A1 | 7/2006 |
| WO | WO-2006073523 A1 | 7/2006 |

OTHER PUBLICATIONS

All Office Actions, Responses and Claims, U.S. Appl. No. 12/758,165.

All Office Actions, Responses and Claims, U.S. Appl. No. 12/758,191.

ABSORBENT ARTICLES COMPRISING WETNESS INDICATORS

CROSS REFERENCE TO RELATED APPLICATIONS

This application is a continuation of, and claims priority to U.S. patent application Ser. No. 12/758,165, filed on Apr. 12, 2010, which claims the benefit of U.S. Provisional Application No. 61/168,756, filed Apr. 13, 2009, the substances of which are incorporated herein by reference.

FIELD OF THE INVENTION

This invention is directed to wetness indicators comprising wetness indicator compositions. Particularly, wetness indication compositions having improved colorant stability.

BACKGROUND OF THE INVENTION

Many disposable absorbent articles comprise a wetness indicator composition. Wetness indicator compositions may comprise a colorant adapted to change in appearance, i.e., appear, disappear, change color, etc., upon contact with liquids such as, urine, runny bowel movements, menses, etc., in the article. Wetness indicating compositions described herein are of the substantially insoluble type such that they are designed so the composition generally remains in the same location of the article before and after being wetted with liquid. Some wetness indicator compositions are intentionally designed to simply disappear into the core of the diaper after being wetted (e.g., wetted with urine). Wetness indicator compositions of the present invention may function to serve the following: 1) the wetness indicator composition should effectively adhere, but not substantially bleed through, to the substrate on which it is applied (e.g., the backsheet) and should possess an optimum balance of cohesive strength and flexibility to remain intact during storage, as well as upon and after being wetted, 2) the initial color of the wetness indicator composition should not prematurely change color such that it confuses the caregiver or wearer as to whether a wetness event has occurred, 3) the color change of the wetness indicator composition should occur as quickly as possible after the wetness event, 4) the contrast in colors between the dry and wetted states of the wetness indicator composition should be great enough to signal the occurrence of the wetness event, 5) the color signaling the wetness event should remain visible for a long period of time after the wetness event and should not migrate to other regions of the diaper such that the signal denoting the wetness event becomes difficult or impossible to interpret, 6) the wetness indicators of the present invention should adhere, but not substantially bleed through, to the substrate that it comes in direct contact with (e.g., the nonwoven dusting layer) or that it is in close proximity to (e.g., the core cover) to provide for adequate wicking of fluid (e.g., urine), 7) the wetness indicator composition should remain stable (i.e., not change color prior to a wetness event) when placed in close proximity (if not direct contact) with higher (versus the colorant of the wetness indicator composition) pH absorbent article components, and 8) the wetness indicator composition should be easily made, easily processed for application onto the wearable article, be safe, and of economical cost.

While problems realized in the past (including high humidity and temperature environments) remain, there are additional challenges associated with new diaper designs, particularly including diaper designs comprising absorbent cores that are substantially cellulose free. These core designs comprise increased levels of absorbent polymer material, adhesives (including, thermoplastic adhesive materials), and surfactants. Each of these comprise chemical compositions that can alter the pH of the wetness indicator composition and thus cause a color change prior to a wetness event. Particularly, alkaline surfactants containing amine, amide, or quaternary functionalities are especially problematic for wetness indicator compositions comprising colorants that change color as the pH rises; but even lower pH moieties like carboxylates can also pose challenges and prematurely activate certain colorants within such wetness indicator compositions.

The color changing active used in many wetness indicator compositions are pH indicators like bromocresol green which changes color from yellow to blue in the pH range of 3.8 to 5.4. To maintain the yellow color of the bromocresol green in the dry state, the wetness indicator composition should be acidic enough to keep it in its yellow state. For a wetness indicator composition containing the bromocresol green pH indicator, it remains yellow up to the point urine contacts it and thereafter turns blue due to the pH increase. In diapers incorporating a wetness indicator composition comprising a colorant that changes color as its pH increases, it is common practice for one to incorporate acids (as well as other chemical components discussed in more detail below) within the wetness indicator composition to maintain the yellow color state of pH indicators, like bromocresol green, prior to a wetness event.

In diaper designs, placing the wetness indicator composition in close proximity to absorbent cores that are substantially cellulose free or comprising high levels of surfactants, there is a desire to optimize the acid content in relation to other materials present in the wetness indicator composition to aid in preventing its premature color change. This is especially true when the diaper design utilizes lower basis weight and more breathable substrates (e.g., backsheets, dusting layers, and core covers) because these substrates allow pH altering chemicals to come in closer proximity with the wetness indicator composition. But, while the acid content is optimized for stability, one also needs to optimize the wetness indicator composition for proper functioning of the other properties (e.g., kinetics, dye retention, stability, adhesion, etc.). If too much acid or too strong of an acid mixture is incorporated, the pH can remain suppressed even after the wetness event such that the yellow color of the bromocresol green, for instance, persists and no blue color (signaling a wetness event) results even when a wetness event has occurred. If too little acid or too weak of an acid mixture is incorporated, the wetness indicator composition can prematurely change color. Thus, the acid content should be optimized so the wetness indicator composition remains stable under various storage scenarios, as well as within new challenging absorbent article designs.

Beyond these stability issues, the wetness indicator composition should adhere to the substrate (e.g., the dusting layer) it faces that is inboard of the wetness indicator to ensure wicking of fluid (e.g., urine) to the wetness indicator composition after a wetness event. That is, when a gap exists between the wetness indicator composition and the inboard substrate (e.g., the dusting layer) that it faces, fluid may not travel from the absorbent core to the wetness indicator within the desired time to signal a wetness event. It may additionally be desired that there is substantial contact/adherence to the substrate it faces to ensure that the wetness indicator composition is evenly (top to bottom and side to side) wetted and thus provides the full signal intended. This can be accomplished by providing a wetness indicator composition that has an optimized "open time" such it is tacky enough, during its incorporation into an absorbent article, for a long enough time to adhere to the substrate, but not so long that it bleeds through the substrate.

Overall, there remains a need for a wetness indicator composition that is stable in the presence of challenging diaper designs, particularly those designs comprising: absorbent cores that are substantially cellulose free and comprising high levels of adhesive (including, thermoplastic adhesive material) and absorbent polymer material, lower basis weight dusting layers and backsheets, and dusting layers and/or core covers coated with surfactants. Particularly, there is a need for more acidic wetness indicator compositions that comprise less phosphorus and/or nitrogen (which correlates to greater colorant stability while still providing acceptable color changing kinetics and retention). Additionally, there is a need for a wetness indicator composition that has an optimized "open time" for use in absorbent articles comprising lower basis weight and breathable films and nonwovens.

SUMMARY OF THE INVENTION

An absorbent article of the present invention may comprise a backsheet, a wetness indicator composition, and an absorbent core. The wetness indicator composition may comprise a stabilizer, a colorant, and a matrix. The absorbent core may comprise a nonwoven layer and an absorbent polymer material, and optionally, a thermoplastic adhesive material. The wetness indicator composition may be in direct contact with an inner surface of the backsheet and an outer surface of the nonwoven layer. And, the absorbent polymer material, and optionally, the thermoplastic adhesive material, may be in direct contact with an inner surface of the nonwoven. Further, the absorbent core may be substantially cellulose free and may be oriented in at least one row.

DETAILED DESCRIPTION OF THE INVENTION

It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

All percentages, ratios and proportions are by weight, and all temperatures are in degrees Celsius (° C.), unless otherwise specified. All measurements are in SI units unless otherwise specified.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer. Absorbent cores that may be used in the present invention are disclosed in US Pub. Nos. 2004/0162536 to Becker filed on Feb. 11, 2004; 2007/0167928 to Becker filed on Mar. 13, 2007; 2007/0179464 to Becker filed on Mar. 13, 2007; 2007/0156108 to Becker filed on Mar. 13, 2007; and 2004/0167486 to Busam filed on Feb. 11, 2004; U.S. Ser. No. 60/936,102 to Hundorf filed on Jun. 18, 2007; 60/936,109 to Hundorf filed on Jun. 18, 2007; 60/936,149 to Hundorf filed on Jun. 18, 2007; 60/936,085 to Ashton filed on Jun. 18, 2007; 60/936,084 to Ashton filed on Jun. 18, 2007; 60/936,150 to Ashton filed on Jun. 18, 2007; 60/936,146 to Asthon filed on Jun. 18, 2007; 60/936,037 to Ashton filed on Jun. 18, 2007; and 61/091,799 to Hundorf filed on Aug. 26, 2008.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wetmilling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants." Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al. on Sep. 28, 1999; and U.S. Ser. No. 11/197,197 to LaVon et al. filed Aug. 4, 2005; Ser. No. 11/224,462 to Lavon et al. filed on Sep. 12, 2005; Ser. No. 11/286,614 to LaVon on Nov. 23, 2005; Ser. No. 11/286,612 to LaVon on Nov. 23, 2005; and Ser. No. 11/709,500 issued to LaVon et al. on Feb. 27, 2007.

Figure 1:
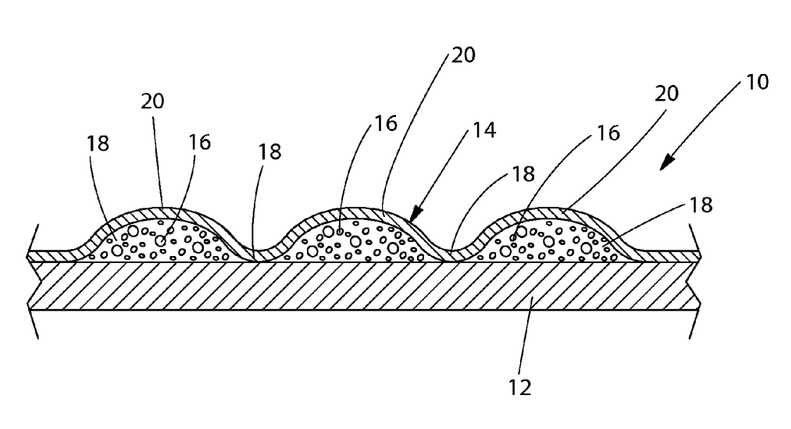
FIG. 1 is a partial longitudinal cross sectional view of an absorbent core (comprising a nonwoven layer and a complex of absorbent polymer material and thermoplastic adhesive material) in accordance with an embodiment of the present invention.

"Substantially cellulose free" is used herein to describe an article component, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core. Substantially cellulose free absorbent cores 10 may comprise absorbent polymer material 16 adhered to the dusting layer (e.g., 12) via thermoplastic adhesive material 18 forming a "complex" 14. The complex 14 may be in rows 20 (see FIG. 1).

"Substantially surfactant free" is used herein to describe an article component, such as a dusting layer, that contains less than 10% by weight of a surfactant or mixture thereof, less than 5% by weight of surfactant, less than 1% by weight of surfactant, no surfactant, or no more than an immaterial amount of surfactant where the surfactant may be anionic, cationic, nonionic, amphoteric or may include mixtures thereof and function to increase the wettability of the article component by reducing the contact angle of synthetic urine (as disclosed in U.S. Pat. No. 6,772,708 to Klofta) in contact with the surface of the article component (e.g., fibers of a nonwoven material or the surface of a film).

"Thermoplastic adhesive material" as used herein is understood to comprise a polymer composition from which fibers are formed and applied to the superabsorbent material with the intent to immobilize the superabsorbent material in both the dry and/or wet state. The thermoplastic adhesive material of the present invention forms a fibrous network over the superabsorbent material. Thermoplastic adhesive material may comprise one or a mixture of adhesives, including, but not limited to polymers such as polybutylene, copolymers such as styrenic block copolymers, tackifying resins, synthetic rubbers like those of the styrene butadiene and carboxylated styrene butadiene types, natural rubbers, waxes such as paraffin and microcrystalline waxes, oils such as mineral oil, anti-oxidants, and the like as is known in the art.

Wetness Indicator Composition

Wetness indicators of the present invention may comprise a wetness indicator composition. The wetness indicator compositions of the present invention comprise a colorant, a matrix, and additional ingredients, all of which are illustrated in more detail herein. Furthermore, the wetness indicator compositions of the present invention may optionally be attached to a substrate, such as, a structural component of a absorbent article. Substrates, disposable absorbent articles and structural components thereof are illustrated in more detail herein.

(a) Colorant

The wetness indicator compositions of the present invention may comprise a colorant. The colorant has an initial color state, which is associated with a first state of the wetness indicator composition. Examples of this first color state include, but are not limited to, colors visible to the human eye, such as, red, blue, green, indigo, violet, yellow, orange, purple, and the like; colors not visible to the human eye, such as, colors visible in the ultra violet (or UV), or infra red (or IR) portion of the electromagnetic spectrum, and the like. The first color state may be invisible, white, black, translucent or opaque. The colorant(s) also has a final color state, which is associated with a second state of the wetness indicator composition. Examples of this second color state include, but are not limited to, colors visible to the human eye, such as, red, blue, green, indigo, violet, yellow, orange, purple, and the like; colors not visible to the human eye, such as, colors visible in the UV, or IR portion of the electromagnetic spectrum, and the like. The second color state may be invisible, white, black, translucent, opaque, or have a change in intensity or visual distinctiveness, and the like, when compared to the first color state. The initial color state of the colorant is different, in some form, to the final color state. For example, the initial color state may be a first color, such as, yellow, while the second color state may be a different color, such as blue; or the initial color state may be a first color, such as, blue, while the second color state may be transparent, such as, a color not visible to the human eye, and only visible in the UV portion of the electromagnetic spectrum.

In the wetness indicator compositions of the present invention, the initial color state is associated with a first state of the wetness indicator composition. This first state of the wetness indicator composition includes, but is not limited to: a specific pH or pH range; absence or presence of a specific compound or compounds, such as, water, urea, dissolved oxygen, ions, such as, but not limited to, iron, calcium, magnesium, zinc, sodium, chloride, protons, hydroxide and combinations thereof, sugars, such as, glucose, enzymes, biological materials in the urine and/or feces; and combinations thereof; microbiological flora and fauna, such as, bacteria and the like; some threshold level of a compound or composition, such as, water, urine etc, below a certain amount; and combinations thereof.

In the wetness indicator compositions of the present invention the final color state is associated with a second state of the wetness indicator composition. This second state of the wetness indicator composition includes, but is not limited to: a specific pH or pH range; absence or presence of a specific compound or compounds, such as, water, urea, dissolved oxygen, ions, such as, but not limited to, iron, calcium, magnesium, zinc, sodium, chloride, protons, hydroxide and combinations thereof, sugars, such as, glucose, enzymes, biological materials in the urine and/or feces; and combinations thereof; microbiological flora and fauna, such as, bacteria and the like; some threshold level of a compound or composition, such as, water, urine, menses, blood and the like; and combinations thereof.

In one embodiment of the present invention, the first state is a specific pH or pH range and the second state is a specific pH or pH range different to the specific pH or pH range of the first state. In one optional embodiment of the present invention the second state is the pH or pH range of urine, preferably human urine, as measured as a neat solution at human body temperature (typically 37.6° C.). The pH or pH range of urine is typically about 5.5 to about 8.0. In this optional embodiment, the first state may be a specific pH or pH range which is more acidic or more basic than the second state, that is, a pH of less than about 5.5 or greater than about 8.0. In one optional embodiment of the present invention, the colorant is a pH indicator. Non-limiting examples of suitable pH indicators include those disclosed in U.S. Pat. No. 6,904,865 to Klofta.

In one optional embodiment of the present invention, the colorant is a sulfonephthalein pH indicator, such as, but not limited to, bromocresol green, bromocresol purple, m-cresol purple, cresol red, chlorophenol red, bromothymol blue, bromopyrogallol red, bromoxylenol blue, bromophenol blue, and combinations thereof. In an acidic state, the sulfonephthalein class of indicators are most commonly yellow in color. Upon contact with liquid, such as urine, having a pH higher than their $pK_a$, the sulfonephthalein class of pH indicators typically change to a green, blue or purple color.

In another optional embodiment of the present invention, the wetness indicator composition may comprise of two or more colorants, each having at least one of their first and second states different, i.e., different $pK_a$ values, a pH and an enzyme trigger, a pH trigger, etc., colors, solubilities, or other properties. The varying first and second states may facilitate interactive scenes, sequences, or displays providing information regarding relative fullness/wetness of the article or merely provide entertainment and/or aesthetic value. For example, the wetness indicating composition may contain one colorant that turns blue and another that turns red upon contact with urine. Alternatively, one portion of the graphic may appear and another portion may disappear upon contact with liquid, such as urine, menses, blood, and the like. Finally, one might include a small quantity of an oil soluble dye like D&C red or D&C yellow to change both the initial and final states of the color for a sulfonephthalein type of pH indicator like bromocresol green. This can lead to color changing combinations which can be more aesthetically pleasing to caregivers.

In another optional embodiment of the present invention the wetness indicator composition may comprise two or more colorants, each having their first and second state the same.

The colorant may be employed in compositions at levels which are effective at indicating the presence of a liquid, and include from about 0.001% to about 5%, from about 0.005% to about 2%, and from about 0.01% to about 1%, and even from 0.01% to 0.5% by weight of the composition.

(b) Matrix

The compositions of the present invention may comprise a matrix comprising first and second binding agents, both of which are illustrated in more detail herein. The matrix acts to hold the colorant in place before, during and after contact with liquid. The matrix of the present invention may be highly resistant to colorant leaching, and may be resistant to premature activation in high humidity environments. Upon contact with liquid, such as urine, menses, blood or the like, the matrix allows sufficient liquid to contact the colorant and effect a change in appearance. The matrix concurrently aids in inhibiting the colorant, in either its initial color state or final color state, from leaching out of the matrix into the surrounding environment, such as, the absorbent core of a disposable absorbent article.

When the wetness indicating composition is attached to a substrate, the matrix and consequently the composition, should have sufficient wet and dry cohesion, adhesion, and/or flexibility to remain fully retained on the substrate. In other words, the composition retains sufficient flexibility, cohesion, and adhesion to prevent portions of the composition from separating, such as, portions of the composition chipping off or flaking off from the rest of the composition and/or the substrate. Thus, the matrix aids in not only preserving and inhibiting the leaching of the colorant, but it also aids in maintaining the structural integrity of the wetness indicator composition in both the dry and wet states.

The matrix, including both the first and second binding agents, may be employed in wetness indicator compositions at levels which are effective at immobilizing and stabilizing the colorant, including from about 5% to about 95%, from about 10% to about 80%, and from about 25% to about 75%, by weight of the composition.

(i) First Binding Agent

The first binding agent may be any material which immobilizes the colorant when the colorant is in its initial color state. There are various materials which may be suitable for use as the first binding agent for the wetness indicating compositions of the present invention. The material selected as the first binding agent will be any material which immobilizes the colorant when in its first color state. In one embodiment of the present invention, possible first binding agents include, but are not limited to, rosins, rosin esters, polymerized rosins, pentaerythritol rosin esters, styrenated terpenes, polyterpene resins, terpene phenolics, and combinations thereof.

A suitable rosin mixture is the combination of Arizona Chemical's Sylvatac RE98 and Sylvaros PR-295. The Sylvatac RE-98 is a pentaerythritol rosin ester and the Sylvaros PR-295 is a polymerized rosin. Both are economical matrix ingredients, both contribute to a darker color in the dry state, both aid in maintaining effective cohesive and adhesive forces, and their acidic nature helps preserve the colorant in its dry state color. In addition to being a suitable first binding agent, rosin esters, polymerized rosins, and pentaerythritol rosin esters may also be a effective solubilizers for some of the other ingredients in these wetness indicating compositions. Furthermore, while not wishing to be limited by theory and as noted, the acidity of some rosin esters, polymerized rosins and pentaerythritol rosin esters is believed to contribute to the stabilization of particular colorants, such as, but not limited to, pH indicators. For example, some of these rosins contain acidic carboxylate groups which aid in keeping a colorant like bromocresol green in its acidic yellow state. This acidic yellow state is the preferred color for the dry state of the wetness indicator composition when a pH indicator like bromocresol green is incorporated into the composition.

The first binding material immobilizes the colorant when in its initial color state. How the first binding material immobilizes to the colorant when in its initial color state depends upon both what the first binding material and colorant are. For example, the first binding agent immobilizes the colorant when the colorant is in its initial color state by one or more forces selected from the group consisting of adhesion, hydrogen bonding, ionic, polar covalent bonding, Van der Waals forces, dipole-dipole forces, London dispersion forces and combinations thereof.

The first binding agent may be employed in compositions at levels which are effective at immobilizing and stabilizing the colorant in its first state, including from about 4% to about 90%, from about 10% to about 75%, and from about 20% to about 65%, by weight of the composition.

(ii) Second Binding Agent

The second binding agent may be any material which immobilizes the colorant when the colorant is in its final color state. There are various materials which may be suitable for use as the second binding agent for the wetness indicating compositions of the present invention.

In one embodiment of the present invention the second binding agents may be selected from, but are not limited to those second binding agents disclosed in U.S. Pat. No. 6,904,865 to Klofta.

In one optional embodiment of the present invention the second binding agent is selected from the group consisting of quaternary ammonium salt compounds, cationic clay, polyacrylic acid polymers, organic acids, and combinations thereof. Examples of suitable quaternary ammonium compounds include, but are not limited to, dimethyl(2-ethylhexylhydrogenatedtallowalkyl) ammonium methyl sulfate, cocoalkylmethyl[ethoxylated(15)] ammonium chloride, dodecyltrimethyl ammonium chloride, hexadecyltrimethyl ammonium methyl sulfate, octadecyltrimethyl ammonium chloride, dicocoalkyldimethly ammonium chloride, di(hydrogenated tallowalkyl)dimethyl ammonium chloride, and distearyldimethyl ammonium chloride.

It should be noted that the counter anion associated with the quaternary compound, or any second binding agent having one or more cationic group, is not specifically limited to chloride. Other anions can also be employed and non-limiting examples include methyl sulfate and nitrite. Similarly, any suitable counter cation, such as, but not limited to, sodium, potassium, calcium, magnesium, zinc, protons, ammonium, substituted ammonium and the like, may be associated with a second binding agent having one or more anionic groups.

The second binding material immobilizes the colorant when in its final color state. How the second binding material immobilizes the colorant when in its final color state depends upon the chemical composition of both the second binding material and colorant. For example, if the colorant's final color state is that of an anionic long chain molecule and the second binding material is a cationic molecule, then the bond formed may be, for example, an ionic bond, a covalent bond, or the like. Another example, if the colorant's final color state is that of a cationic molecule, and the second binding material is an anionic long chain molecule, then the bond formed may be, for example, an ionic bond, covalent bond, or the like.

In one embodiment of the present invention the second binding agent immobilizes the colorant when the colorant is in its final color state by one or more selected from the group consisting of covalent bonding, ionic bonding, Van der Waals, and combinations thereof.

Without wishing to be bound by theory, it is believed that when the colorant is an anion in its final color state and the second binding agent is a cation or the colorant is a cation in its final color state and the second binding agent is an anion, the second binding agent forms an ionically bonded coacervate with the colorant. For example, when the final state associated with a colorant's final color state is the pH of urine, contacting the colorant with urine will change the colorant to its final color state, i.e., an anion, and this forms an ionic bond with the second binding agent, which is a cation. The coacervate formation is due to the strong coulombic interaction between the opposite charges of the colorant and the second binding agent. The coacervate formed between the colorant and the second binding agent neutralizes the charge in both species and dramatically reduces both of their solubilities in polar solvents such as water or urine while the coacervate's solubility in the matrix remains high due to this charge neutralization and the coacervate's more lipophilic nature. Both of these effects dramatically inhibits the leaching of the colorant from the matrix. The increased lipophilicity of the coacervate leads to increased intermolecular bonding forces between the coacervate and components of the matrix. These intermolecular forces may further limit the diffusion and mobility of the colorant into an aqueous environment such as urine.

In certain optional embodiments of the present invention, use of cationic quaternary ammonium compounds as the second binding agent may also function to darken or intensify the color change of certain colorants, especially those belonging to the sulfonephthalein class of pH indicators. Without wishing to be bound by theory, it is believed this darkening is due to several possible factors: 1) alkaline impurities within the quaternary ammonium raw material, 2) absorption shifting and absorptivity coefficient increases due to coacervate formation and/or 3) increased formation of the colorant in its final color state.

The second binding agent may be employed in compositions at levels which are effective at immobilizing the colorant in its second state, including from about 0.5% to about 20%, from about 0.5% to about 10%, and from about 0.1% to about 5%, by weight of the composition.

Stabilizer Ingredient

Wetness indicator compositions of the present invention may include a stabilizer. It may be desirable to include a stabilizer when the colorant is a pH indicator and when the absorbent article could be stored under conditions of high humidities and temperatures. The inclusion of a stabilizer within the wetness indicator composition is also especially important for new diaper designs where materials and/or chemicals are present that could potentially prematurely activate the color change of the colorant within the wetness indicator composition.

In one embodiment of the present invention, the stabilizer is an acidic stabilizer. In another embodiment of the present invention, the stabilizer is a basic stabilizer. The inclusion of a stabilizer, while not wishing to be limited by theory, is believed to play a role in stabilizing the colorant against premature changes caused by exposure to humid environments and/or certain components of the diaper, by maintaining a stable pH, such as a low pH environment with an acidic stabilizer, around the colorant even when the system is exposed to high humidities and/or certain components of the diaper. This maintenance of a stable pH environment keeps the colorant, especially when the colorant is a pH indicator, in its initial dry color state.

One of the key properties of a properly functioning wetness indicator is for it to maintain its dry state color during a variety of storage and packaging conditions while still undergoing a noticeable color change in a reasonable amount of time after being contacted by urine. The colorant should also remain stable to various chemicals and materials that might be present in the diaper. Although acidic moieties present in the rosins as part of the matrix can aid in preserving the dry state color, additional stabilizer ingredients have been found to be necessary with some new diaper designs where high pH components within the diaper can cause the undesirable and premature color change activation of the colorant. To maintain the colorant in its acidic dry state color, acids of suitable strength should be added. Suitable strength is defined by the colorant and pH range where it changes color.

For a pH indicator colorant like the sulfonephthalein class which includes bromocresol green which changes color between a pH of 3.8 and 5.4 (see "The Sigma-Aldrich Handbook of Stains, Dyes and Indicators," by Floyd J. Green, Aldrich Chemical Co., Milwaukee, Wis.), the stabilizer should contribute suitably strong acidic moieties to keep the bromocresol green in its yellow state within the matrix. Although many strong acids like sulfuric acid and hydrochloric acid have suitably low pH's to accomplish this, their solubilities are low in these anhydrous matrices. In addition, their high acidity can chemically decompose the structures of some of the components present in the wetness composition and diaper. As noted, carboxylic acid moieties present in the matrix ingredients like rosins can also aid in maintaining the colorant in its acidic color state but carboxylic acids are typically too weak to maintain the dry yellow state of bromocresol green if it is exposed to high humidities and/or high pH components within new diaper designs. To increase the strength of the carboxylic acids, one can add electron withdrawing groups between the carboxylic acid moiety and another portion of the molecule. Although a fatty acid like stearic acid can aid in preserving the dry state color, it can be made more effective by making it a stronger acid by inserting polyoxyethylene groups between the carboxylic acid group and the alkyl chain. These types of molecules are called ether carboxylates and these acidic molecules can be effective in maintaining the dry state acid form of the pH indicator colorant like bromocresol green. In addition, the alkyl group present in these ether carboxylates increases their solubility in the wetness indicator matrix. Finally, the ether carboxylate's surfactancy can aid in increasing the kinetics for activating the color change of the wetness indicator composition after it is contacted by urine.

Other suitable stabilizers are those of the monoalkyl phosphate free acid and dialkyl phosphate free acid types. The phosphate acid moiety is a stronger acid than the carboxylic acid group and thus can be more effective in maintaining the low pH environment required to keep the pH indicator colorant in its dry acidic state. These alkyl phosphate free acids have been found to be particularly effective in preserving the dry state color of the bromocresol green colorant from premature activation as caused by high humidities or destabilizing materials and/or chemicals present in new diaper designs. Particularly effective alkyl phosphate free acids are stearyl phosphate free acid, cetyl phosphate free acid, and cetearyl phosphate free acids. Thus, the phosphate is a suitably strong acid to maintain the pH indicator colorant in its acidic dry state form, and the lipophilic alkyl moiety aids in increasing its solubility within the wetness indicator composition. In addition, the surfactant nature of the alkyl phosphate free acids can aid in speeding up the kinetics of the color change after the wetness indicator composition is contacted by urine.

Other acidic stabilizers which are particularly effective in stabilizing the wetness indicator formula to high humidities and/or destabilizing components within the diaper include, but are not limited to: organic acids, such as, but not limited to, fatty acids such as stearic acid, palmitic acid, lower molecular weight acids such as citric acid, malic acid, maleic acid, lactic acid, glycolic acid, gluconic acid, fumaric acid, adipic acid, ascorbic acid, and salicylic acid; acid esters, such as, citrate esters, e.g., monostearyl citrate and monocetyl citrate, glycolate esters, lactate esters; phosphorus containing organic acids, such as, monostearyl phosphate and monocetyl phosphates; ether carboxylic acids; N-acyl sarcosinic acids; N-acyl glutamic acids; N-acyl ethylenediaminetriacetic acid; alkane sulfonic acids; alpha-olefin sulfonic acids; alpha-sulfonic acid fatty acid methyl esters; sulfate esters; inorganic acids, such as, phosphoric acid; and combinations thereof. Examples of suitable basic stabilizers include, but are not limited to: monoethanolamine; diethanolamine; triethanolamine; dipropylenetriamine; diiosopropyl amine; organic diamines, such as, but not limited to, 1,3-bis(methylamine)-cyclohexane, 1,3-pentanediamine; inorganic bases, such as, but not limited to, sodium hydroxide, magnesium hydroxide, and combinations thereof.

The stabilizer, when present is typically employed in compositions at levels which are effective at stabilizing the colorant, from about 0.001% to about 30%, from about 0.1% to about 15%, and also from about 1% to about 10%, by weight of the composition.

Optional Additional Ingredients

In one optional embodiment of the present invention, the wetness indicator composition may include optional ingredients, including, but not limited to, surfactants, structural adjuncts, and combinations thereof. The optional additional ingredients, when present, are typically employed in compositions at levels which are effective at providing the benefits of the optional additional ingredient or ingredients, including from about 0.001% to about 50%, from about 0.1% to about 40%, and from about 1% to about 35%, by weight of the composition. The optional ingredients and amounts disclosed in U.S. Pat. No. 6,904,865, issued Jun. 14, 2005 to Klofta, et al. may be used in the wetness indicator compositions of the present inventions.

Substrate

In one embodiment of the present invention, the wetness indicator composition of the present invention may be on and/or in a substrate. When present on a substrate, the wetness indicator composition will typically be placed on and/or in a substrate where the substrate will be contacted by a liquid, such as water, urine, menses, blood and the like. The substrate may include, but is not limited to, woven fabrics, nonwoven fabrics, films, sponges, and combinations thereof. The substrate may comprise synthetic and/or natural materials. In one embodiment of the present invention the optional substrate may be an article in its own right, such as, a continuous nonwoven fabric. In another embodiment of the present invention the substrate to which the wetness indicator may be applied or otherwise affixed comprises any one, or a combination of, structural components of an absorbent article, including, but not limited to, the backsheet, topsheet, fasteners, absorbent material, etc., or may be a separate element added or applied to the product. In one optional embodiment of the present invention the wetness indicator composition is applied to the absorbent article as a whole.

The manufacture of substrates, absorbent articles and structural components thereof, for use herein form no part of this invention. The following discussion is for convenience of formulation, but is not intended to limit the type of substrate used herein.

In one embodiment of the present invention the disposable absorbent article is a disposable diaper. Typically, modern disposable diapers comprise a liquid pervious topsheet a liquid impervious backsheet; an absorbent core which may be positioned between at least a portion of the topsheet and the backsheet; side panels; elasticized leg cuffs; an elastic waist feature; and a fastening system. In one embodiment opposing sides of the disposable diaper may be seamed or welded to form a pant. This allows the article to be used as a pull-on type diaper, such as a training pant. Additional illustrative, but non-limiting, information on construction, assembly, and the various components (including backsheets, dusting layers, upper and lower covering sheets, and webs) of disposable diapers may be found in U.S. Pat. No. 3,860,003 to Buell; U.S. Pat. No. 5,151,092 to Buell; U.S. Pat. No. 5,221,274 to Buell; U.S. Pat. No. 5,554,145 to Roe et al. on Sep. 10, 1996; U.S. Pat. No. 5,569,234 to Buell et al.; U.S. Pat. No. 5,580,411 to Nease et al.; U.S. Pat. No. 6,004,306 to Robles et al.; U.S. Pat. No. 5,938,648 to LaVon et al.; U.S. Pat. No. 5,865,823 to Curro; U.S. Pat. No. 5,571,096 to Dobrin et al.; U.S. Pat. No. 5,518,801 to Chappell, et al.; U.S. Pat. No. 4,573,986 to Minetola et al.; U.S. Pat. No. 3,929,135, to Thompson; U.S. Pat. No. 4,463,045 to Ahr, et al.; U.S. Pat. No. 4,609,518 to Curro et al.; U.S. Pat. No. 4,629,643 to Curro et al.; U.S. Pat. No. 5,037,416 to Allen et al.; U.S. Pat. No. 5,269,775 to Freeland et al.; U.S. Pat. No. 4,610,678 to Weisman et al.; U.S. Pat. No. 4,673,402 to Weisman et al.; U.S. Pat. No. 4,888,231 to Angstadt; U.S. Pat. No. 5,342,338 to Roe; U.S. Pat. No. 5,260,345 to DesMarais et al.; U.S. Pat. No. 5,026,364 to Robertson; U.S. Pat. No. 3,848,594 to Buell; U.S. Pat. No. 4,846,815 to Scripps; U.S. Pat. No. 4,946,527 to Battrell; U.S. Pat. No. 4,963,140 to Robertson et al.; U.S. Pat. No. 4,699,622 to Toussant et al.; U.S. Pat. No. 5,591,152 to Buell et al.; U.S. Pat. No. 4,938,753 to Van Gompel, et al.; U.S. Pat. No. 5,669,897 to LaVon, et al.; U.S. Pat. No. 4,808,178 to Aziz et al.; U.S. Pat. No. 4,909,803 to Aziz et al.: U.S. Pat. No. 4,695,278 to Lawson and U.S. Pat. No. 4,795,454 issued to Dragoo; and U.S. Ser. No. 10/770,043 to LaVon; U.S. Pat. No. 7,318,820 to LaVon et al.; U.S. Pat. No. 6,962,578 to LaVon; U.S. Pat. No. 7,377,914 to LaVon; Ser. No. 11/715,976 to LaVon; Ser. No. 10/880,128 to LaVon; Ser. No. 11/131,799 to LaVon et al., Ser. No. 11/133,818 to LaVon et al.; Ser. No. 11/135,689 to LaVon; Ser. No. 11/140,888 to LaVon et al.; Ser. No. 11/158,563 to LaVon et al.; Ser. No. 11/159,916 to LaVon et al., Ser. No. 11/197,197 to LaVon et al.; Ser. No. 11/210,345 to LaVon et al.; Ser. No. 11/224,462 to LaVon et al.; Ser. No. 11/231,511 to LaVon et al.; Ser. No. 11/231,512 to LaVon et al.; Ser. No. 11/231,500 to LaVon et al.; U.S. Pat. No. 7,320,684 to LaVon et al.; Ser. No. 11/286,934 to LaVon et al.; Ser. No. 11/286,614 to LaVon; Ser. No. 11/286,612 to LaVon; Ser. No. 11/700,585 to LaVon et al.; Ser. No. 11/709,500 to LaVon et al.; Ser. No. 11/713,906 to LaVon; Ser. No. 11/728,127 to LaVon et al.; 61/073,154 to LaVon; and 61/073,169 to LaVon; US Pub. Nos. 2004/0162536 to Becker filed on Feb. 11, 2004; 2007/0167928 to Becker filed on Mar. 13, 2007; 2007/0179464 to Becker filed on Mar. 13, 2007; 2007/0156108 to Becker filed on Mar. 13, 2007; and 2004/0167486 to Busam filed on Feb. 11, 2004; U.S. Ser. No. 60/936,102 to Hundorf filed on Jun. 18, 2007; 60/936,109 to Hundorf filed on Jun. 18, 2007; 60/936,149 to Hundorf filed on Jun. 18, 2007; 60/936,085 to Ashton filed on Jun. 18, 2007; 60/936,084 to Ashton filed on Jun. 18, 2007; 60/936,150 to Ashton filed on Jun. 18, 2007; 60/936,146 to Asthon filed on Jun. 18, 2007; 60/936,037 to Ashton filed on Jun. 18, 2007; and 61/091,799 to Hundorf filed on Aug. 26, 2008.

In one alternative embodiment of the present invention a portion of the absorbent article, such as part or all of the topsheet, part or all of the barrier leg cuffs and the like, may be optionally coated with a lotion, as is known in the art. Examples of suitable lotions include, but are not limited to, those described in U.S. Pat. No. 5,607,760 to Roe on; U.S. Pat. No. 5,609,587 to Roe; U.S. Pat. No. 5,635,191 to Roe et al.; U.S. Pat. No. 5,643,588 to Roe et al.; and U.S. Pat. No. 5,968,025 to Roe et al.

The wetness indicator may be applied to a substrate via any means of liquid or semi-liquid application as known in the art, including, but not limited to, slot coating, spraying, gravure printing, ink jet printing, and digital printing. Alternatively, the wetness indicator may be a solid or semi-solid material affixed to a substrate via adhesive bonding, chemical bonding or intermolecular force bonding. Multiple indicators may be applied to the same substrate in overlapping or non-overlapping geometries. The solidification process may be accelerated via the use of convective mass transport, if evaporation of a solvent is required, or convective or conductive heat transfer, e.g., cooling via air or chilled rolls, etc.

As briefly described in the Background of the Invention above, the wetness indicator composition should not only adhere to the substrate (e.g., backsheet) to which it initially applied, but the wetness indicator composition should adhere to the substrate (e.g., the dusting layer) it faces that is inboard of the wetness indicator to ensure wicking of fluid (e.g., urine) to the wetness indicator composition after a wetness event. That is, when a gap exists between the wetness indicator composition and the inboard substrate (e.g., the dusting layer) that it faces, fluid may not travel from the absorbent core to the wetness indicator within the desired time to signal a wetness event.

It may additionally be desired that there is substantial contact/adherence to the substrate it faces to ensure that the wetness indicator composition is evenly (top to bottom and side to side) wetted and thus provides the full signal intended. This can be accomplished by providing a wetness indicator composition that has an optimized "open time" such it is tacky enough for a long enough time to adhere to the substrate, but not so long that it bleeds through the substrate.

Bleeding through becomes a larger issue when the substrate is a lower basis weight and/or breathable film or nonwoven. Absorbent articles of the present invention may use backsheets having a basis weight less than about 60 gsm, less than about 40 gsm, or less than about 20 gsm. Said backsheets may be breathable, having water vapor transmission rates (according to ASTM E-96/E-96M-05) greater than about 100 $g/m^2/24$ hr (grams of water vapor per square meter per 24 hour period), greater than about 1000 $g/m^2/24$ hr, or greater than about 5000 $g/m^2/24$ hr. The backsheets of the present invention may be a single layer or may be a laminate and may comprise polypropylene and/or polyethylene.

Further, nonwoven dusting layers (as well as, intermediary layers between the wetness indicator composition and the dusting layer) of the present invention may have a mean flow pore (according to ASTM F316-86) size of greater than about 1 micron, greater than about 10 microns, or greater than about 100 microns. And may have a hydrohead value of greater than about 1 mm of water, greater than about 10 mm of water, or greater than about 100 mm of water as measured by AATCC 127-1985 titled "Rising Column Strike Through." And, nonwovens and intermediary layers may have a basis weight of less than about 50 g/m$^2$, less than about 30 g/m$^2$, or less than about 15 g/m$^2$. Nonwovens and intermediary layers of the present invention may comprise fibers having a diameter of less than about 200 microns, less than about 20 microns, or less than about 2 microns. And, the fibers may be shaped (i.e., having a non-round cross-section), including multilobal (e.g., bilobal, trilobal fibers, etc.).

In embodiments where the wetness indicator composition is in direct contact with the outboard face (outer face) of the dusting layer, the dusting layer may have a complex of thermoplastic adhesive material and absorbent polymer material adhered to the inboard face (inner face) of the dusting layer. In such an embodiment, the area of the inner face of the dusting layer directly opposite the outer face of the dusting layer that is adhered to the wetness indicator composition (i.e., the area the inner face of the dusting layer directly across from the wetness indicator composition) may be from about 0.01 cm$^2$ to about 200 cm$^2$, from about 1 cm$^2$ to about 50 cm$^2$, or from about 3 cm$^2$ to about 20 cm$^2$. And, the amount of the complex of thermoplastic adhesive material and absorbent polymer material adhered to inner face of the dusting layer in the area the inner face of the dusting layer directly across from the wetness indicator composition may be from about 1 g/m$^2$ to about 300 g/m$^2$, from about 10 g/m$^2$ to about 200 g/m$^2$, or from about 25 g/m$^2$ to about 150 g/m$^2$. This is the complex of thermoplastic adhesive material and absorbent polymer material largely responsible for prematurely changing the color of the wetness indicator composition.

Wetness indicator compositions that may be used with the lower basis weight and/or breathable films and nonwovens above may comprises straight chain alkyl moieties (which is correlated with "open time") having a chain length from about C12 to about C300, from about C14 to about C100, or from about C16 to about C50. Further, wetness indicator compositions of the present inventions may have a basis weight greater than about 10 g/m$^2$, greater than about 20 g/m$^2$, or greater about 25 g/m$^2$. Further more, wetness indicator compositions of the present invention may, according to the Wetness Indicator Sample Test (Phosphate) (according to ASTM D-809) below, have a phosphorus content of 10.0% or less, of 1.0% or less, or of 0.1% or less. And wetness indicator compositions of the present invention may, according to the Wetness Indicator Sample Test (Nitrogen) (according to ASTM D-3228(2008)) below, have a nitrogen content of 3.0% or less, of 0.3% or less, or of 0.03% or less.

In one embodiment, the wetness indicator composition may initially be applied to an inboard face (i.e., the inner face, relative to the wearer) of the backsheet such that it adheres to the backsheet. Then the outboard face (i.e., the outer face, relative to the wearer) dusting layer comes in contact with wetness indicator composition such that it adheres to the dusting layer over the entire (or substantially entire) inboard surface of the wetness indicator composition.

The wetness indicator composition when present on a substrate may provide for a signal visible from outside the substrate, while the product is being worn, e.g., visible to the wearer, a caregiver, parent and the like. That is, the wetness indicator compositions are affixed to the substrate at a portion which enables it to be in fluid communication with the liquid, e.g., urine, menses, blood and the like, and allows the change initial color state to its final color state to visible to an observer. For example, color or contrast change, is visible through the substrate and/or the absorbent article, such as, the of backsheet or garment-facing covering of a disposable diaper article, which is also in fluid communication with the liquid, such as urine menses, blood and the like, deposited in the absorbent core of the substrate and/or the absorbent article.

In one optional embodiment of the present invention, the change of the colorant from its initial color state to its final color state is visible within a short time after the wetness indicator composition is contacted with a liquid, e.g., urine, menses, blood and the like. In one alternative embodiment of the present invention, the change of the colorant from its initial color state to its final color state is visible within about 15 minutes, or within about 5 minutes after a liquid, such as urine, menses, blood and the like, contacts the wetness indicator composition.

In another optional embodiments of the present invention, the substrate, or absorbent article comprising the substrate may be designed to allow liquid, such as urine, menses, blood, and the like, to contact the wetness indicator composition in certain regions of the substrate, or absorbent article at various loading levels. For example, a disposable diaper may be designed to allow urine to contact the wetness indicator composition located in the crotch region of the product on the first urination, but contact the wetness indicator composition in other regions of the disposable diaper only after the amount of urine in the disposable diaper reaches a predetermined threshold value. For example, the absorbent core of the disposable diaper may have limited ability to distribute urine from a given region of the disposable diaper until it contains sufficient urine to change the colorant in a wetness indicator from its initial color state to its final color state in this region, thereby preventing change of the wetness indicator composition in adjacent regions of the article until the overall urine loading in the disposable diaper increases above a given level. As the total urine loading in the disposable diaper increases, more regions of the disposable diaper will contain sufficient urine to change the colorant in a wetness indicator that may be located in those regions from its initial color state to its final color state.

The wetness indicator compositions may be present on a substrate in any desired pattern or configuration, including, but not limited to, stripes, dots, geometric shapes, irregular shapes, alphanumeric characters, pictorial representation of animals, pictorial representation of inanimate objects, cartoon characters, anthropomorphic images, logos, trademarks and any combination or arrangement thereof. The wetness indicating compositions may be applied in any pattern or in conjunction with permanent graphics, such as, permanent graphics on the outer surfaces of a disposable absorbent article.

In one embodiment of the present invention, the wetness indicator compositions, when present on a substrate, is typically employed at levels which are effective at providing visible signals, including from about 1 g per square meter (gsm) to about 100 gsm, from about 5 gsm to about 75 gsm, and from about 10 gsm to about 60 gsm. However, it is to be understood that the amount of wetness indicator present on a substrate will depend upon many factors, such as but not limited to, substrate type (e.g., thick, thin, opacity, bulky, dense, other physical properties etc.), substrate material, intended use of the substrate (e.g., disposable diaper, panty liner, bandage etc.), method used for applying the wetness indicator compositions, desired intensity of signal in either dry or after contacting liquid, desired kinetics for the color change, desired stability of the color within the wetness indicator composition, desired pattern or configuration of the wetness indicator composition on substrate, and combinations thereof.

Additional information on incorporation of wetness indicating compositions in and/or on substrates and/or disposable absorbent articles can be found disclosed in U.S. Pat. No. 4,022,211 issued, on May 10, 1977, to Timmons; U.S. Pat. No. 6,297,42, issued on Oct. 2, 2001, to Olson; U.S. Pat. No. 6,307,119 issued on Oct. 23, 2001 to Cammarota; and U.S. Patent Applications Nos. 20020007162A1 entitled "Absorbent articles having wetness indicating graphics incorporating a training zone," filed on Aug. 13, 2001, published Jan. 17, 2002, in the name of Cammarota; and 20010053898A1 entitled "Absorbent articles having wetness indicating graphics providing an interactive training aid" filed on Jul. 24, 2001, published Dec. 20, 2001, in the name of Olson; and WO 00/76438 published on Dec. 21, 2000, and assigned to Kimberly-Clark Worldwide Inc., and WO 00/76443 published on Dec. 21, 2000, and assigned to Kimberly-Clark Worldwide Inc.

Test Methods

A. Controlled Temperature and Humidity (CTH) Stability Test Method:

Wetness indicators, according to this method, are first made by heating up the wetness indicator composition about 10° C. above its melting point. For the compositions in the Examples A-H below, this temperature is in the range of about 95° C. to about 105° C. At this same temperature, a stainless steel bird applicator (Gardco Model Number AP-6X002ts or equivalent, Gardco Incorporated, Pompano Beach, Fla.) with a width of 4" to 6" and a gap of 0.002" is also heated. On a flat and level lab bench is placed a series of up to 10 polypropylene backsheet films with a basis weight of approximately 18 gsm with dimensions of around 3" by 8". These 10 backsheet films are separated by about 2" from one another and each is taped to the lab bench with transparent tape running across the top most edge of each film.

After taping the backsheet films to the lab bench, insulated gloves are placed on one's hands and used to remove the hot wetness indicator composition from the oven and place it in the vicinity near the top most edge of the backsheet film. The hot bird applicator is also removed from the oven and placed near the top most edge of the backsheet with its long dimension running parallel to the short 3" dimension of the backsheet film and its legs resting firmly on the lab bench rather than on the backsheet film itself. Next, the hot wetness indicator composition is dispensed along the front edge of the bird applicator and while firmly holding the left and right legs of the bird applicator with downward pressure, one firmly moves the bird applicator in the direction of the long dimension of the backsheet film while maintaining the bird applicator's long dimension parallel to the short width dimension of the backsheet film.

One can vary the basis weight of the wetness indicators applied to the backsheet by changing the viscosity of the wetness indicator composition, by applying the composition at different temperatures, by changing the speed at which the bird applicator is dragged across the backsheet film, or by varying the gap of the bird applicator.

The basis weight of the wetness indicator composition applied to the backsheet film can be calculated by cutting out the wetness indicator of known dimensions and weighing it on a balance. The basis weight of the wetness indicator composition and backsheet film combination is calculated by dividing the weight of the backsheet film in units of grams by its area using the units of $m^2$. The basis weight unit of grams per square meters is typically abbreviated as gsm or $g/m^2$. To calculate the basis weight of the wetness indicator applied to the backsheet film, one must then subtract the basis weight of the backsheet film from the basis weight calculated for the wetness indicator composition applied to the backsheet film.

For the wetness indicators prepared in this manner, one can typically prepare a variety of wetness indicator basis weights ranging from 10 gsm to 100 gsm. As noted, these range of basis weights can be made by varying the speed at the which the bird applicator is dragged across the backsheet film, changing the temperature of the composition, using a different gap setting for the applicator, or altering the other variables mentioned above.

After the wetness indicators are prepared and the basis weights calculated, they are applied to the dusting layer of a substantially cellulose free core by firmly pressing them onto the core with the wetness indicator side in direct contact with the dusting layer of the substantially cellulose free core. The wetness indicators can be firmly applied to the dusting layer using a roller made with a hard plastic or wood material. Typically, one tries to apply a variety of basis weight wetness indicators to the dusting layer side of the core in order to study the effect of basis weight on such properties like stability, kinetics, and colorant retention.

After the wetness indicators have been applied to the dusting layer of the substantially cellulose free core, they are placed dusting layer side up in a controlled temperature and humidity room which is controlled to a humidity of 75% and a temperature of 40° C. The time and date at which the wetness indicators are placed in the room is recorded, and the samples are periodically checked for any premature color changing activity. For bromocresol green containing compositions, such as Examples A-H, the initial and stable dry state color is yellow. Any color change observed for these bromocresol green containing compositions wetness indicator compositions using digital photography and by use of the following 6-point scale of 0 to 5:

"0" corresponds to no color change of the wetness indicator through the backsheet film remaining, such that the wetness indicator remains completely yellow over the backsheet film area corresponding to the wetness indicator area;

"1" corresponds to the presence of green or blue regions over less than 10% of the backsheet film area corresponding to the wetness indicator area;

"2" corresponds to the presence of green or blue regions over 10% to 40% of the backsheet film area corresponding to the wetness indicator area;

"3" corresponds to the presence of green or blue regions over 41% to 60% of the backsheet film area corresponding to the wetness indicator area;

"4" corresponds to the presence of green or blue regions over 61% to 90% of the backsheet film area corresponding to the wetness indicator area; and "5" corresponds to the presence of green or blue regions over greater than 90% of the backsheet film area corresponding to the wetness indicator area.

The wetness indicators, through the backsheet films, are photographed or graded in this manner for storage up to 12 months in this or other controlled temperature and humidity rooms.

B. Colorant Kinetics Test Method:

After the wetness indicators are made (they are in the form of a film) and applied to the substantially cellulose free cores as described above in the CTH stability test, the diapers the wetness indicators have been incorporated into can be tested to determine how quickly the wetness indicators change from their stabilized dry state color to their wet state color after synthetic urine contacts the wetness indicator film. For wetness indicators with wetness indicator compositions containing only bromocresol green, the dry state color is yellow and the wet state color is blue. The wetness indicators applied to the dusting layer of the substantially cellulose free core should approximately mimic both the basis weight and dimensions of the wetness indicators that would be marketed to consumers. Thus, a basis weight of 20 gsm to 60 gsm would be most appropriate with dimensions of approximately 5 millimeters in width by 160 milliliters in length. This wetness indicator should be applied to the dusting layer such that is its long dimension is parallel to the long dimension of the diaper. And, it should also be applied on the outside face of the dusting layer such that it runs along the center of the core of the diaper.

First, the diaper comprising the wetness indicator is placed with the wetness indicator side down (topsheet side up) on a clear, transparent, and colorless piece of polycarbonate with dimensions approximating 14" long by 6" wide by 0.25" thick. This polycarbonate sheet on which the diaper sits is then supported on both ends with legs to which a mirror is attached. The mirror is angled at 45 degrees and sits directly below the sample so one can view the wetness indicator side of the diaper during this colorant kinetics test.

Another clear, transparent, and colorless polycarbonate sheet is then placed on the topsheet side of the diaper. A round hole of 1 inch in diameter is cut into this polycarbonate sheet with its center located in the middle of the 6 inch width dimension and 5 inches from one of the edges in the 14 inch long dimension. Onto this hole, a 3 inch long and clear, transparent polycarbonate cylinder is attached which has a round hole diameter of 1 inch (which is made to overlap the 1 inch round hole in the polycarbonate sheet) and a wall thickness of 0.25 inches.

This top polycarbonate sheet is placed on top of the diaper so the center of the polycarbonate cylinder sits on top of the core in a location designed to accept the initial urination event. After placing this polycarbonate sheet on the diaper, two 6.5 pound weights are placed on either end of the sheet in order to mimic the weight of the baby on top of the diaper.

Synthetic urine is then prepared according to the following recipe as disclosed in U.S. Pat. No. 6,772,708 to Klofta. The synthetic urine is then heated to a temperature of 38° C. in order to mimic body temperature of urine. 40 milliliters of this heated synthetic urine is then measured into a graduated cylinder. This 40 milliliters of the synthetic urine is then poured into the polycarbonate cylinder on top of the diaper at a rate of approximately 2 to 3 milliliters per second. After all of synthetic urine is poured into the cylinder, a stop watch is started. An additional forty milliliters is poured into the cylinder at a rate of approximately 2 to 3 milliliters per second at both the 5 and 10 minute time points as measured using the stop watch.

The color of the wetness indicator is then monitored (as can be seen through the backsheet) at the following time points after the stop watch is started after the first 40 milliliter volume of synthetic urine is poured into the cylinder: 1) 2 minutes and 2) 5 minutes. After the second dose of 40 milliliters of synthetic urine is added at the 5 minute point, observations are recorded at the 10 minute point, and after the third dosed of 40 milliliters is added at the 10 minute point, final observations are recorded at the 15 minute point. The color can be measured using the following 6-point scale of 0 to 5:

0 denotes no color change of the wetness indicator through the backsheet film remaining in its dry state color, such that the wetness indicator remains completely yellow over the backsheet film area corresponding to the wetness indicator area;

1 denotes less than 10% of the backsheet film area corresponding to the wetness indicator area changing to the wet state color;

2 denotes 10-40% of the backsheet film area corresponding to the wetness indicator area changing to the wet state color;

3 denotes 41-60% of the backsheet film area corresponding to the wetness indicator area changing to the wet state color;

4 denotes 61-90% of the backsheet film area corresponding to the wetness indicator area changing to the wet state color; and 5 denotes greater than 90% of the backsheet film area corresponding to the wetness indicator area changing to the wet state color.

C. Colorant Retention Test Method:

The colorant retention test is performed on the identical diaper used in the colorant kinetic test. The diaper comprising the wetness indicator continues to be sandwiched between the polycarbonate sheets described in the colorant kinetic test method (above) and continues to be weighted down for a total of 2 to 16 hours.

After this range of time is met, the time is recorded and the diaper is flipped over so the wetness indicator side faces up for easy viewing by the naked eye. Both the color of the wetness indicator (as viewed through the backsheet), as well as the areas located next to it are inspected to determine dye retention within the wetness indicator, as well as dye leaching into areas residing next to the wetness indicator. Even though the color could be measured spectrophotometrically, a visual grading system can also be applied. The color of wetness indicator can be graded according to the following scale:

0 denotes less than 10% of final wet state color residing within the wetness indicator through the backsheet film;

1 denotes 10% to 50% of the final wet state color remaining within the wetness indicator through the backsheet film 2 denotes 51% to 90% of the final wet state color remaining within the wetness indicator through the backsheet film; and 3 denotes greater than 90% of the final wet state color remaining within the wetness indicator through the backsheet film.

Any colorant leaching into the surrounding areas in the vicinity of the wetness indicator is simply recorded with a yes or no designation. A "yes" denotes the observation of some of the wet state color residing in the areas around the wetness indicator. A "no" denotes the presence of no wet state color within the surrounding areas.

EXAMPLES A-H

| Component | A | B | C | D | E | F | G | H |
|---|---|---|---|---|---|---|---|---|
| First Binding Agent[1] | 33.00 | 33.01 | 32.76 | 32.95 | 32.61 | 34.40 | 58.8 | 48.8 |
| First Binding Agent[2] | 15.00 | 15.01 | 14.93 | 15.01 | 14.81 | 15.57 | — | — |
| HLB Modifier[3] | 19.03 | 18.99 | 19.06 | 19.03 | 18.96 | 19.42 | 16.0 | 16.0 |
| Stabilizer[4] | 3.41 | 3.41 | 3.17 | 2.95 | 2.85 | 2.08 | 5.0 | 9.0 |
| Stabilizer[5] | 0.20 | — | — | — | — | — | — | — |
| Second Binding agent[6] | 1.00 | 1.00 | 1.13 | 0.81 | 0.99 | 1.04 | 1.0 | 1.0 |
| Second Binding agent[7] | — | — | — | — | 1.95 | 2.01 | 3.0 | 3.0 |
| Colorant[8] | 0.18 | 0.18 | 0.20 | 0.20 | 0.20 | 0.20 | 0.20 | 0.2 |
| Colorant[9] | — | — | — | 0.02 | — | — | — | — |
| Surfactant[10] | 27.78 | 28.01 | 28.44 | 28.52 | 27.37 | 24.98 | 12.0 | 18.0 |
| Anti-Oxidant[11] | 0.40 | 0.39 | 0.31 | 0.51 | 0.26 | 0.30 | 0.3 | 0.3 |
| CTH Stability Test (5 days at 75% Relative Humidity & 40° C.) | 0 | 1 | 1 | 1 | 2 | 3 | 4 | 3 |
| Colorant Kinetics Test (at 5 minutes) | 4 | 4 | 4 | 4 | 4 | 4 | 3 | 3 |
| Colorant Retention Test (at 4 hours) | 2 | 2 | 2 | 2 | 3 | 3 | 4 | 4 |
| Wetness Indicator Sample Test (Phosphate) (%) | 0.33 | 0.33 | 0.31 | 0.28 | 0.27 | 0.20 | 0.48 | 0.87 |
| Wetness Indicator Sample Test (Nitrogen) (parts per million) | 320 | 320 | 360 | 260 | 840 | 870 | 1120 | 1120 |

[1]Pentaerythritol Rosin Ester, (Sylvatac RE 98 from Arizona Chemical, Jacksonville, FL)
[2]Polymerized Rosin (Sylvaros PR-295 from Arizona Chemical, Jacksonville, FL)
[3]W835 Microcrystalline Wax from Crompton, Petrolia, PA)
[4]Cetyl Phosphate Free Acid (Hostaphat CC-100 from Clariant)
[5]Anhydrous Citric Acid, (EMD)
[6]Cocoalkylmethyl[ethoxylated(15)] ammonium chloride (Ethoquad C/25) from Akzo Incorporated, Chicago, IL).
[7]Dimethyl(2-ethylhexylhydrogenated tallowalkyl)ammonium methyl sulfate, (HTL8(W)-MS) from Akzo Incorporated, Chicago, IL)
[8]Bromocresol Green, Free Acid from Curtiss Labs, Bensalem, PA
[9]D&C Red #17 (Sensient Inc.)
[10]$C_{20}$-$C_{40}$ Pareth-10 (Performathox 450 from New Phase Incorporated, Sugar Land, TX)
[11]Irganox 1010FF from Ciba, Each of the Examples A-H are made by mixing the HLB modifier and viscosity modifier and heating the mixture at 100° C. until completely melted. Reduce the heat on this HLB/Viscosity modifier premix to 95° C. and maintain mixing. In another clean, glass container, mix the first binding agent, stabilizer, and the surfactant. Heat and stir this mixture at 90° C. until completely melted. Add in the HLB/Viscosity modifier premix to the mixture of first binding agent/stabilizer/surfactant and heat and mix at 90° C. Add to this mixture the second binding agent and mix until the temperature reaches 90° C. Finally, add to this mixture the colorant and mix for approximately 1 hour at 90° C. until the mixture is clear, transparent and light orange in color.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a backsheet;
   a wetness indicator composition comprising a stabilizer, a colorant, and a matrix;
   an absorbent core comprising a nonwoven layer and a complex of absorbent polymer material and thermoplastic adhesive material;
   wherein the wetness indicator composition is in direct contact with an inner surface of the backsheet and an outer surface of the nonwoven layer;
   wherein the complex of absorbent polymer material and thermoplastic adhesive material is in direct contact with an inner surface of the nonwoven layer;
   wherein the absorbent polymer material is disposed in rows, wherein the rows run longitudinally;
   wherein the colorant has a pH lower than a pH of the complex of absorbent polymer material and thermoplastic adhesive material;
   wherein the stabilizer has a pH lower than the pH of the colorant; and
   wherein the stabilizer has a weight percent concentration greater than a weight percent concentration of the colorant.

2. The absorbent article of claim 1, wherein the wetness indicator composition comprises materials selected from the group consisting of quaternary ammonium salt compounds, ethoxylated quaternary ammonium salt compounds, propoxylated quaternary ammonium salts, alkyl diammonium pentamethyl chlorides, quarternized silicone compounds, cationic guars, cationic exchange resins, cationic clay materials, amines, ethoxylated amines, propoxylated amines, polyamines, amine oxides, amides, polyethyleneimines, anionic exchange resins, polyacrylic acid polymers, organic acids, rosins, rosin esters, pentaerythritol rosin esters, polymerized rosins, dyes, pigments, an HLB modifier, a surfactant, an anti-oxidant, viscosity modifiers, hardening agents, and combinations thereof.

3. The absorbent article of claim 1, wherein the wetness indicator composition comprises straight chain alkyl moieties having a chain length from about C12 to about C300.

4. The absorbent article of claim 1, wherein the colorant is a pH indicator.

5. The absorbent article of claim 1, wherein the colorant is selected from the group consisting of bromocresol green, bromocresol purple, bromophenol blue, m-cresol purple, cresol red, chlorophenol red, bromothymol blue, bromopyrogallol red, bromoxylenol blue, acridine, acridine orange, oil soluble dyes, pigments, and combinations thereof.

6. The absorbent article of claim 1, wherein the backsheet comprises polypropylene, polyethylene, or combinations thereof.

7. The absorbent article of claim 1, wherein the backsheet has a water vapor transmission rate greater than about 100 g/m2/24 hrs.

8. The absorbent article of claim 1, wherein the backsheet has a basis weight greater than about 5 g/m2.

9. The absorbent article of claim 1, wherein the wetness indicator composition is affixed to the backsheet.

10. The absorbent article of claim 1, wherein the wetness indicator composition is affixed to the nonwoven layer of the absorbent core.

11. The absorbent article of claim 1, wherein the wetness indicator is affixed to the backsheet in one or more patterns selected from the group consisting of stripes, dots, geometric shapes, irregular shapes, alphanumeric characters, anthropomorphic images, pictorial representation of animals, pictorial representation of inanimate objects, cartoon characters, logos, trademarks and combinations thereof.

12. The absorbent article of claim 1, wherein the nonwoven layer is a dusting layer.

13. The absorbent article of claim 1, wherein the nonwoven layer is surfactant free.

14. The absorbent article of claim 1, wherein the dusting layer has a mean flow pore size greater than about 1 micron.

15. The absorbent article of claim 1, wherein the dusting layer has a basis weight greater than about 3 g/m$^2$.

16. The absorbent article of claim 1, wherein the dusting layer has a hydrohead greater than about 1 mm of water.

17. The absorbent article of claim 1, wherein the dusting layer has a fiber diameter greater than about 10 nanometers.

18. The absorbent article of claim 1, wherein the dusting layer comprises fibers having a non-round cross-section.

19. The absorbent article of claim 1, wherein the colorant has an initial color state, the initial color state being associated with a first state of the wetness indicator composition and a final color state, the final color state being associated with a second state of the wetness indicator composition.

20. The absorbent article of claim 19, wherein the matrix comprises a mixture of a first binding agent and a second binding agent, wherein the first binding agent immobilizes the colorant when it is in its initial color state and the second binding agent immobilizes said colorant when it is in its final color state.

21. An absorbent article comprising:
a backsheet;
a wetness indicator composition comprising a stabilizer, a colorant, and a matrix;
an absorbent core comprising absorbent polymer material;
a nonwoven layer between the absorbent core and the backsheet;
wherein the wetness indicator composition is in direct contact with an inner surface of the backsheet and an outer surface of the nonwoven layer;
wherein the absorbent polymer material is in direct contact with an inner surface of the nonwoven layer;
wherein the absorbent core is substantially cellulose free and comprises at least one longitudinally oriented row of the absorbent polymer material;
wherein the colorant has a pH lower than a pH of the absorbent polymer material;
wherein the stabilizer has a pH lower than the pH of the colorant; and
wherein the stabilizer has a weight percent concentration greater than a weight percent concentration of the colorant.

* * * * *